(12) United States Patent
Nageshwar (10) Patent No.: US 10,052,257 B2
(45) Date of Patent: Aug. 21, 2018

(54) METHOD AND APPARATUS FOR STIMULATIVE ELECTROTHERAPY

(71) Applicant: DyAnsys, Inc., San Mateo, CA (US)

(72) Inventor: Srini Nageshwar, Los Gatos, CA (US)

(73) Assignee: DYANSYS, INC., San Mateo, CA (US)

( * ) Notice: Subject to any disclaimer, the term of this patent is extended or adjusted under 35 U.S.C. 154(b) by 0 days.

(21) Appl. No.: 13/916,934

(22) Filed: Jun. 13, 2013

(65) Prior Publication Data

US 2014/0371820 A1    Dec. 18, 2014

(51) Int. Cl.
| | |
|---|---|
| *A61N 1/36* | (2006.01) |
| *A61H 39/00* | (2006.01) |
| *A61B 5/00* | (2006.01) |
| *A61B 5/053* | (2006.01) |

(52) U.S. Cl.
CPC ......... *A61H 39/002* (2013.01); *A61B 5/0531* (2013.01); *A61B 5/4035* (2013.01); *A61B 5/6815* (2013.01); *A61N 1/36017* (2013.01); *A61H 2201/5005* (2013.01); *A61H 2201/5007* (2013.01); *A61H 2201/5097* (2013.01); *A61H 2205/027* (2013.01); *A61N 1/36053* (2013.01)

(58) Field of Classification Search
CPC ................. A61H 39/002; A61H 39/08; A61H 2205/027; A61N 1/0502; A61N 1/0558; A61N 1/36014; A61N 1/36017; A61N 1/36114; A61N 1/37211
USPC ................. 607/2, 46, 60, 115, 149; 128/907
See application file for complete search history.

(56) References Cited

U.S. PATENT DOCUMENTS

| | | |
|---|---|---|
| 524,660 A | 8/1894 | Woodward |
| 3,646,606 A | 2/1972 | Buxton et al. |
| 3,872,252 A | 3/1975 | Malchman et al. |
| 3,939,841 A | 2/1976 | Dohring et al. |
| 4,244,375 A | 1/1981 | Farrar et al. |
| 4,262,672 A | 4/1981 | Kief |
| 4,428,380 A | 1/1984 | Wong et al. |
| 4,677,984 A | 7/1987 | Sramek |
| 4,685,466 A | 8/1987 | Rau |
| 4,784,162 A | 11/1988 | Ricks et al. |

(Continued)

FOREIGN PATENT DOCUMENTS

| | | |
|---|---|---|
| AT | 150525 | 4/1937 |
| CH | 239028 | 9/1945 |

(Continued)

OTHER PUBLICATIONS

International Search Report for PCT application PCT/US2013/045712 (dated Apr. 9, 2014).

(Continued)

*Primary Examiner* — Allen Porter, Jr.
(74) *Attorney, Agent, or Firm* — Alston & Bird LLP (57) ABSTRACT

An electrical apparatus includes a battery, a circuit adapted to generate a periodic signal, and a wireless radio transceiver. The electrical apparatus further includes a control circuit adapted to set a characteristic of the periodic signal. The characteristic is received by an input of the wireless radio transceiver. The electrical apparatus further includes a first electrically conductive electrode adapted to electrically contact and puncture a first portion of a surface when the periodic signal is injected below the first portion of the surface. The periodic signal is coupled to the first electrically conductive electrode.

20 Claims, 7 Drawing Sheets

(56) References Cited

U.S. PATENT DOCUMENTS

| | | |
|---|---|---|
| 5,012,816 A | 5/1991 | Lederer |
| 5,058,605 A | 10/1991 | Slovak |
| 5,269,302 A | 12/1993 | Swartz et al. |
| 5,285,793 A | 2/1994 | Slovut et al. |
| 5,324,287 A | 6/1994 | Szeles |
| 5,349,962 A | 9/1994 | Lockard et al. |
| 5,449,378 A | 9/1995 | Schouenborg |
| 5,578,065 A | 11/1996 | Hattori et al. |
| 5,645,070 A | 7/1997 | Turcott |
| 5,772,688 A | 6/1998 | Muroki |
| 5,823,788 A | 10/1998 | Lemelson et al. |
| 5,957,862 A | 9/1999 | Lu et al. |
| 5,957,951 A | 9/1999 | Cazaux et al. |
| 5,971,922 A | 10/1999 | Arita et al. |
| 6,117,075 A * | 9/2000 | Barnea ............... 600/300 |
| 6,445,955 B1 | 9/2002 | Michelson et al. |
| 6,493,592 B1 | 12/2002 | Leonard et al. |
| 6,539,264 B1 | 3/2003 | Bishay et al. |
| 6,735,471 B2 | 5/2004 | Hill et al. |
| 6,999,445 B1 | 2/2006 | Dmitriev et al. |
| 7,092,849 B2 * | 8/2006 | Lafitte ............ A61B 5/02405 702/183 |
| 7,336,993 B1 | 2/2008 | Szeles |
| 7,660,637 B2 | 2/2010 | Szeles |
| 7,797,041 B2 * | 9/2010 | Libbus et al. ............ 607/2 |
| 8,868,199 B2 | 10/2014 | Kaula et al. |
| 2002/0013613 A1 * | 1/2002 | Haller et al. ............ 607/60 |
| 2002/0077560 A1 * | 6/2002 | Kramer ............ A61B 5/0428 600/509 |
| 2003/0236469 A1 | 12/2003 | Hedgecock |
| 2004/0210261 A1 * | 10/2004 | King et al. ............ 607/9 |
| 2006/0064139 A1 * | 3/2006 | Chung et al. ............ 607/45 |
| 2006/0074337 A1 | 4/2006 | Yoo et al. |
| 2006/0122675 A1 | 6/2006 | Libbus et al. |
| 2006/0195164 A1 | 8/2006 | Sondergaard et al. |
| 2006/0202805 A1 | 9/2006 | Schulman et al. |
| 2007/0179816 A1 | 8/2007 | Lemme et al. |
| 2007/0219455 A1 | 9/2007 | Wong et al. |
| 2007/0239210 A1 | 10/2007 | Libbus et al. |
| 2008/0071188 A1 | 3/2008 | Home et al. |
| 2008/0249439 A1 | 10/2008 | Tracey et al. |
| 2008/0262376 A1 | 10/2008 | Price |
| 2008/0275468 A1 | 11/2008 | Chuang et al. |
| 2008/0288016 A1 | 11/2008 | Amurthur et al. |
| 2009/0105605 A1 | 4/2009 | Abreu |
| 2009/0171420 A1 * | 7/2009 | Brown et al. ............ 607/60 |
| 2009/0181353 A1 | 7/2009 | Dasgupta |
| 2009/0292180 A1 | 11/2009 | Mirow et al. |
| 2009/0326595 A1 * | 12/2009 | Brockway et al. ............ 607/3 |
| 2010/0168822 A1 * | 7/2010 | Szeles ............ 607/72 |
| 2010/0198142 A1 | 8/2010 | Sloan et al. |
| 2010/0286734 A1 | 11/2010 | Yun et al. |
| 2011/0007950 A1 | 1/2011 | Deutsch |
| 2011/0028860 A1 | 2/2011 | Chenaux et al. |
| 2011/0071418 A1 | 3/2011 | Stellar et al. |
| 2011/0167103 A1 | 7/2011 | Acosta et al. |
| 2011/0238083 A1 | 9/2011 | Moll et al. |
| 2011/0319966 A1 | 12/2011 | Sadkhin |
| 2012/0053648 A1 | 3/2012 | Neher et al. |
| 2012/0075464 A1 | 3/2012 | Derenne et al. |
| 2012/0101358 A1 | 4/2012 | Boettcher et al. |
| 2012/0226333 A1 * | 9/2012 | Szeles ............ 607/59 |
| 2012/0277833 A1 | 11/2012 | Gerber et al. |
| 2013/0093829 A1 | 4/2013 | Rosenblatt et al. |
| 2013/0096641 A1 | 4/2013 | Strother et al. |
| 2013/0117669 A1 | 5/2013 | Shikhman et al. |
| 2014/0370476 A1 | 12/2014 | Nageshwar |
| 2014/0371608 A1 | 12/2014 | Nageshwar |
| 2014/0371621 A1 | 12/2014 | Nageshwar |
| 2014/0371820 A1 | 12/2014 | Nageshwar |
| 2016/0113526 A1 | 4/2016 | Nageshwar et al. |
| 2017/0143247 A1 | 5/2017 | Nageshwar |

FOREIGN PATENT DOCUMENTS

| | | |
|---|---|---|
| CH | 620821 | 12/1980 |
| CN | 1443329 A | 9/2003 |
| CN | 1788265 A | 6/2006 |
| DE | 319602 | 8/1914 |
| DE | 29720785 | 2/1998 |
| EP | 0229200 | 7/1987 |
| EP | 0759307 | 2/1997 |
| FR | 969374 | 12/1950 |
| FR | 1297117 | 5/1962 |
| FR | 2345994 | 10/1977 |
| FR | 2354759 | 1/1978 |
| GB | 1514079 | 6/1978 |
| GB | 1603726 | 11/1981 |
| GB | 2115700 | 9/1983 |
| JP | 04-314459 | 11/1992 |
| SU | 957917 | 9/1982 |
| SU | 1296164 | 3/1987 |
| WO | WO 2000/074331 | 12/2000 |
| WO | WO 2005/001706 | 1/2005 |
| WO | WO2010/014259 | 2/2010 |
| WO | WO 2012/078924 A1 | 6/2012 |
| WO | WO 2014/200488 A1 | 12/2014 |
| WO | WO 2014/200489 A2 | 12/2014 |
| WO | WO 2014/200492 A1 | 12/2014 |
| WO | WO 2014/200498 A1 | 12/2014 |

OTHER PUBLICATIONS

International Search Report for PCT application PCT/US2013/045587 (dated Sep. 19, 2013).

International Search Report for PCT application PCT/US2013/045668 (dated Sep. 27, 2013).

Lafitte et al. "Towards assessing the sympathovagal balance," Medical and Biological Engineering and Computing vol. 44, Issue 8, pp. 675-682 (Aug. 2006).

Schondorf et al. "Sympathovagal Balance," Poster #44 23rd International Symposium on the Autonomic Nervous System Atlantis Resort, Paradise Island, Bahamas (Nov. 2012).

International Search Report for PCT application PCT/US2013/045588 (dated Jan. 10, 2014).

Non-Final Office Action for U.S. Appl. No. 13/917,471 dated Sep. 22, 2014, 11 pages.

WIPO Application No. PCT/162003/002522, PCT International Search Report dated Feb. 9, 2004.

Abarbanel, H.D.I, "The analysis of observed chaotic data in physical systems," Reviews of Modern Physics, American Physical Society, 65(4):1331-1392, (1993).

Morfill et al., "Komplexitatsanalyse in der Kardiologie," Physikalische Blater, 50(2):156-160, (1994).

U.S. Appl. No. 10/961,710, Non-Final Office Action dated Dec. 2, 2005.

U.S. Appl. No. 10/961,710, Notice of Allowance dated Apr. 17, 2006.

U.S. Appl. No. 13/916,944, Final Office Action dated Dec. 10, 2015.

U.S. Appl. No. 13/916,994, Non-Final Office Action dated Apr. 30, 2015.

U.S. Appl. No. 13/916,944, Non-Final Office Action dated Aug. 11, 2016.

U.S. Appl. No. 13/916,975, Final Office Action dated Aug. 4, 2016.

U.S. Appl. No. 13/916,975, Non-Final Office Action dated Jun. 2, 2015.

U.S. Appl. No. 13/917,471, Advisory Action dated May 10, 2016.

U.S. Appl. No. 13/917,471, Final Office Action dated Feb. 20, 2015.

U.S. Appl. No. 13/917,471, Final Office Action dated Feb. 26, 2016.

U.S. Appl. No. 13/917,471, Non-Final Office Action dated Aug. 12, 2015.

WIPO Application No. PCT/US2013/045587, PCT International PReliminary Report on Patentability dated Dec. 15, 2015.

WIPO Application No. PCT/US2013/045587, PCT Written Opinion of the International Searching Authority dated Sep. 19, 2013.

WIPO Application No. PCT/US2013/045588, PCT International Preliminary Report on Patentability dated Dec. 12, 2015.

(56) References Cited

OTHER PUBLICATIONS

WIPO Application No. PCT/US2013/045588, PCT Written Opinion of the International Searching Authority dated Jan. 10, 2014.
WIPO Application No. PCT/US2013/045668, PCT International Preliminary Report on Patentability dated Dec. 15, 2015.
WIPO Application No. PCT/US2013/045668, PCT Written Opinion of the International Searching Authority dated Sep. 27, 2013.
WIPO Application No. PCT/US2013/045712, PCT International Preliminary Report on Patentability dated Dec. 15, 2015.
WIPO Application No. PCT/US2013/045712, PCT Written Opinion of the International Searching Authority dated Apr. 9, 2014.
EPO Application No. EP13886840, Supplementary European Search Report dated Feb. 3, 2017.
EPO Application No. EP13886698, Supplementary European Search Report dated Mar. 20, 2017.
EPO Application No. EP13886872, Supplementary European Search Report dated May 30, 2017.
EPO Application No. EP13887010, Supplemental European Search Report dated May 30, 2017.
U.S. Appl. No. 13/916,944, Final Office Action dated May 12, 2017.
U.S. Appl. No. 13/916,944, Advisory Action dated Aug. 17, 2017.
U.S. Appl. No. 13/916,944, Non-Final Office Action dated Nov. 8, 2017.

\* cited by examiner

METHOD AND APPARATUS FOR STIMULATIVE ELECTROTHERAPY

CROSS-REFERENCES TO RELATED APPLICATIONS

This application is related to U.S. Pat. No. 7,092,849, titled "EXTRACTING CAUSAL INFORMATION FROM A CHAOTIC TIME SERIES," granted Aug. 15, 2006, the content of which is incorporated herein by reference in its entirety. This application is also related to the following applications filed herewith: U.S. patent application Ser. No. 13/917,471, titled "STIMULATIVE ELECTROTHERAPY USING AUTONOMIC NERVOUS SYSTEM CONTROL," U.S. patent application Ser. No. 13/916,944, titled "METHOD AND APPARATUS FOR AUTONOMIC NERVOUS SYSTEM SENSITIVITY-POINT TESTING", and U.S. patent application Ser. No. 13/916,975, titled "COMPUTER IMPLEMENTED TRAINING OF A PROCEDURE," the contents of all of which are incorporated herein by reference in their entirety.

BACKGROUND

The present invention relates generally to a method and apparatus for applying an electrical signal to a patient, and in particular, for applying a time varying signal to a nervous system of a patient.

Measures of heart rate variability have been shown to be a powerful means of assessing the influence of the autonomic nervous system on the cardiac system. Indeed, the autonomic nervous system, with its sympathetic and parasympathetic, hereinafter also referred to as "vagal" subsystems, governs involuntary actions of the cardiac muscle and every visceral organ in the body.

The autonomic nervous system is not directly accessible to voluntary control. Instead, it operates in an autonomic fashion on the basis of autonomic reflexes and central control. One of its major functions is the maintenance of homeostasis within the body. The autonomic nervous system further plays an adaptive role in the interaction of the organism with its surroundings.

In many diseases, the sympathetic and/or parasympathetic parts of the autonomic nervous system are affected leading to autonomic dysfunction. It is then important to have reliable and representative measures of the activity and the state of the autonomic nervous system.

U.S. Pat. No. 7,092,849 to Lafitte, et al. describes a method, a system, and a computer code for analyzing the state of the autonomic nervous system from a time-varying signal representing a chaotic series of time intervals between quasi-periodical events produced by the cardiac system governed by the autonomic system. Thus, real-time monitoring of the sympathovagal balance between the parasympathetic and the sympathetic components of the autonomic nervous system is possible.

The autonomic nervous system plays an important role in pain modulation and perception and chronic pain is likely due to a malfunction in the body's central nervous system. While there are many medications and physical therapies that are used to treat pain, they do not cure it and only mask the pain response, sometimes with undesired side effects such as with narcotic medications.

A point stimulation device is a non-narcotic combination of permanent acupuncture-like needles and electrical stimulation used to treat chronic pain over time. A point stimulation device uses auricular acupuncture as a treatment based on normalizing the body's dysfunction through stimulation of points on the ear. The resulting amelioration of pain and illness is believed to be through the reticular formation and the sympathetic and parasympathetic nervous systems. Specific points in the ear are related to major organs in the body. However, existing medical devices and treatment protocols for testing and locating sensitivity-points on the skin surface for point stimulation needle insertion have not taken advantage of the capabilities of real-time sympathovagal balance monitoring. Present point stimulation devices provide only a fixed electrical stimulation signal.

BRIEF SUMMARY

According to one embodiment of the present invention, an electrical apparatus includes a battery, a circuit adapted to generate a periodic signal, and a wireless radio transceiver. The electrical apparatus further includes a control circuit adapted to set a characteristic of the periodic signal. The characteristic is received by an input of the wireless radio transceiver. The electrical apparatus further includes a first electrically conductive electrode adapted to electrically contact and puncture a first portion of a surface when the periodic signal is injected below the first portion of the surface. The periodic signal is coupled to the first electrically conductive electrode.

According to one embodiment, the electrical apparatus further includes a second electrically conductive electrode adapted to electrically contact but not puncture a second portion of the surface. The second electrically conductive electrode provides a direct electrical contact between the second electrically conductive electrode and the second portion of the surface, which provides a return signal path for the periodic signal when the periodic signal is injected below the first portion of the surface.

According to one embodiment, the electrical apparatus further includes a housing having an insulating surface and at least a first orifice in the insulating surface. The first electrically conductive electrode is adapted to be located outside the housing and coupled through the first orifice to the circuit. The housing encloses the battery and the circuit.

According to one embodiment, the housing is adapted to have a shape being adapted to conform to a third portion of the surface when the periodic signal is injected below the first portion of the surface. According to one embodiment, the housing is adapted to hermetically seal the electrical apparatus.

According to one embodiment, the wireless radio transceiver operates on a transmission standard selected from one of Bluetooth®, 6LoWPAN®, ZigBee®, DASH7®, Z-Wave®, MiWi®, or OSION®. According to one embodiment, the characteristic is selected from one of a frequency, an amplitude, a pulse shape, or a duty cycle.

According to one embodiment, the periodic signal is an electrotherapy signal. The characteristic of the periodic signal is adapted to stimulate a response in a parasympathetic nervous system of a patient. The surface is a skin of the patient when the periodic signal is injected below the first portion of the surface. According to one embodiment, the frequency of the periodic signal is set to a predetermined frequency associated with a treatment of a patient.

According to one embodiment of the present invention, a method for signal injection includes providing a battery, providing a wireless radio transceiver, and providing a first electrically conductive electrode. The method further includes generating a periodic signal in time from a circuit, receiving a characteristic of the periodic signal by an input of the wireless transceiver, and setting the characteristic via a control circuit. The method further includes coupling the periodic signal to the first electrically conductive electrode, and electrically contacting and puncturing a first portion of a surface when the periodic signal is injected below the first portion of the surface.

According to one embodiment, the method further includes contacting but not puncturing a second portion of the surface by a second electrically conductive electrode. The second electrically conductive electrode provides a direct electrical contact between the second electrically conductive electrode and the second portion of the surface, thereby providing a return signal path for the periodic signal when the periodic signal is injected below the first portion of the surface.

According to one embodiment, the method further includes providing a housing having an insulating surface and at least a first orifice in the insulating surface, and locating the first electrically conductive electrode outside the housing. The method further includes coupling the first electrically conductive electrode through the first orifice to the circuit, and enclosing the battery and the circuit with the housing.

According to one embodiment, the method further includes shaping the housing to conform to a third portion of the surface when the periodic signal is injected below the first portion of the surface. According to one embodiment, the method further includes hermetically sealing the electrical apparatus with the housing.

According to one embodiment, the method further includes selecting the characteristic from one of a frequency, an amplitude, a pulse shape, or a duty cycle. According to one embodiment, the method further includes setting the frequency of the periodic signal to a predetermined frequency associated with a treatment of a patient.

A better understanding of the nature and advantages of the embodiments of the present invention may be gained with reference to the following detailed description and the accompanying drawings.

DETAILED DESCRIPTION

The present invention relates generally to a method and apparatus for testing a patient's skin, and in particular, to testing a patient's skin to find autonomic nervous system sensitivity-points. Auricular acupuncture electrotherapy treatments involve inserting an electrotherapy needle into the skin of a patient at certain sensitivity-points on the ear associated with a particular therapy regimen and applying an electrotherapy signal to the electrotherapy needle. Finding a location to place the needle may be determined by foreknowledge of general locations and testing or measuring local skin resistance. However, electrotherapy treatment acts through the autonomic nervous system so skin resistivity alone may not be the best test indicator for electrotherapy needle placement.

In accordance with one embodiment of the present invention, a test and measurement for electrotherapy needle placement may generate and apply an electrical signal similar or identical to the electrotherapy signal that would be used during treatment to a portion of the patient's skin surface without puncturing the skin. The skin surface is then probed with the electrotherapy signal via an electrically conductive tip, to identify a location that stimulates a vagal response of the patient's autonomic nervous system by monitoring the sympathovagal balance. The identified location may then be pricked by an electrotherapy needle which is then connected to the electrotherapy signal for a long duration treatment period. Locating the needle sites initially may not constitute therapy but may improve the outcome of planned acupuncture electrotherapy.

Figure 1:
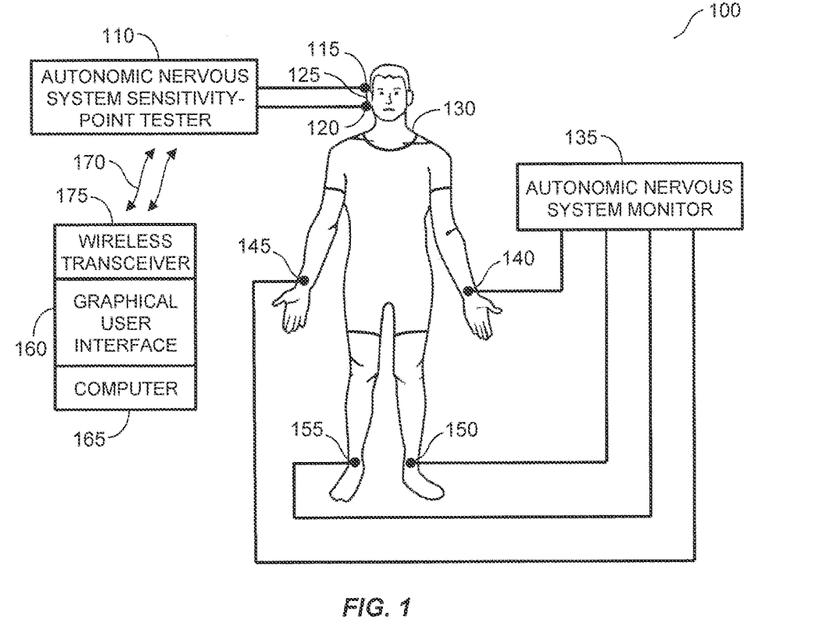
FIG. 1 depicts a simplified block diagram of a patient testing theatre, in accordance with one embodiment of the present invention.

FIG. 1 depicts a simplified block diagram of a patient testing theatre 100, in accordance with one embodiment of the present invention. Patient testing theatre 100 includes an autonomic nervous system sensitivity-point tester 110 coupled to an electrically conductive tip 115 and an electrode 120, which in-turn are connected to an ear 125, hereinafter also referred to as "portion of skin", of a patient 130. In one embodiment, an autonomic nervous system monitor 135 is coupled to electrodes 140, 145, 150, 155 respectively on the patient's left arm, right arm, left leg, right leg to receive quasi-periodical electro cardiogram signals from the cardiac system that are in-turn governed by the patient's autonomic nervous system. The patient is preferably in a supine position on an examination table in a clinical environment for autonomic nervous system testing and monitoring.

In the exemplary embodiment depicted in FIG. 1, the patient is represented as a human. It is understood, however, that the patient may be any living creature possessing an autonomic nervous system and cardiac system. In the exemplary embodiment depicted in FIG. 1, autonomic nervous system sensitivity-point tester 110 is shown as connecting to an ear. It is understood, however, that autonomic nervous system sensitivity-point tester 110 may instead be connected to any portion of skin demonstrated to have nerve connections sensitive enough to affect the autonomic nervous system of the patient.

In one embodiment, the patient testing theatre 100 may include a graphical user interface 160 coupled to a computer 165, which may be coupled via cable (not shown) or via wireless radio transmission 170 to autonomic nervous system sensitivity-point tester 110. Preferably, the autonomic nervous system sensitivity-point tester is a wireless hand held device, which may be programmed or have certain characteristics set by a medical practitioner or technician (not shown) via graphical user interface 160 and computer 165. In one embodiment, computer 165 may be a desktop, laptop, pad, mini-pad, or smart phone that may have a wireless transceiver 175.

The autonomic nervous system monitor 135 is adapted to convert the patient's electro cardiogram signals to, among other information, a sympathovagal balance between the parasympathetic and the sympathetic components of the autonomic nervous system. U.S. Pat. No. 7,092,849 to Lafitte, et al. and co-pending U.S. patent, titled "STIMULATIVE ELECTROTHERAPY USING AUTONOMIC NERVOUS SYSTEM CONTROL" to Nageshwar, which are incorporated by reference, describe, in part, the theory of operation for autonomic nervous system monitor 135.

Figure 2:
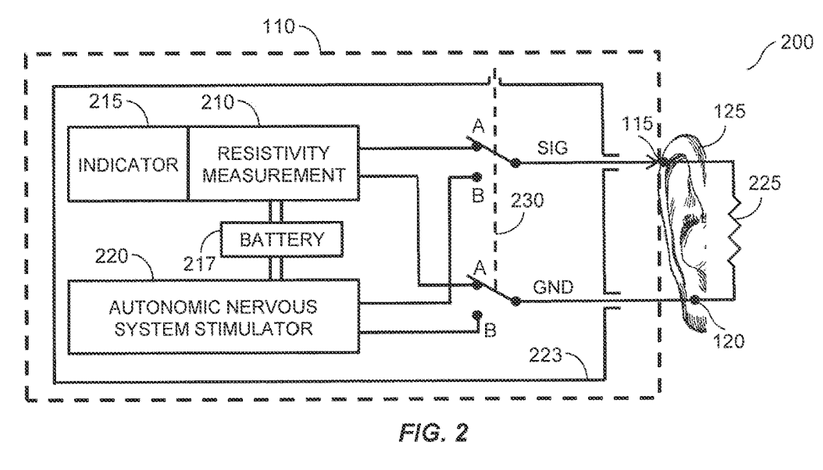
FIG. 2 depicts a simplified block diagram of the autonomic nervous system sensitivity-point tester and the portion of the patient's skin represented in FIG. 1, in accordance with one embodiment of the present invention.

FIG. 2 depicts a simplified block diagram of autonomic nervous system sensitivity-point tester 110 and portion of the patient's skin 125 represented in FIG. 1, in accordance with one embodiment of the present invention. FIG. 2 depicts autonomic nervous system sensitivity-point tester 110, hereinafter also referred to as "circuit", which includes a resistivity measurement unit 210, an indicator 215, an autonomic nervous system stimulator 220, a switch 230, an electrically conductive tip 115, a battery 217, a housing 223, and an electrode 120. Resistivity measurement 210 couples to indicator 215. Battery 217 provides portable power to the circuit and enables hand-held operation.

Resistivity measurement 210 is adapted to generate an electrical resistance measuring signal to measure a skin resistivity 225 coupled between electrically conductive tip 115 and electrode 120 when the patient is tested. Indicator 215 is responsive to a value of electrical resistance measured by the circuit and may provide a visual indicator, a sonic indicator, and/or a vibrational indicator. For example, indicator 215 may be a buzzer that changes sound pitch in relation to the measured value of skin resistivity 225, which may change as electrically conductive tip 115 is moved around by the medical practitioner to contact different portions of the patient's skin surface.

Autonomic nervous system stimulator 220 is adapted to generate an electrotherapy signal, hereinafter also referred to as "periodic signal" or "periodic signal in time," coupled to electrically conductive tip 115 that stimulates a vagal response of the patient's autonomic nervous system when the patient is tested. Electrically conductive tip 115 provides electrical contact to but does not puncture a portion of the skin surface of the patient when the patient is tested.

Electrode 120 is applied to a different portion of skin than that portion of skin surface being tested to optimize electrotherapy needle placement. Electrode 120 is adapted to be a return signal path, i.e. ground, for either the electrical resistance-measuring signal or the electrotherapy signal thereby enabling a gloved medical practitioner, hereinafter also referred to as "tester" to facilitate applying the electrical resistance measuring signal or the electrotherapy signal to the patient. Electrode 120 may be a portion of metal foil taped temporarily on the patient's skin or an electrotherapy needle temporarily placed in the patient's skin.

Housing 223 may have an insulating surface and at least one orifice in the insulating surface through which electrically conductive tip 115 protrudes or extends outside the housing. Housing 223 may enclose battery 217 and the circuit. The housing may have a shape that may be adapted to be hand held when the skin surface is tested. In other words, the housing is shaped to fit the hand grasp of a person using autonomic nervous system sensitivity-point tester 110. The insulating surface of the housing may have other orifices for example to allow a tester to operate switch 230 and for electrode 120. Housing 223 may hermetically seal the circuit and seal the orifices, for example by using a flexible gasket around the electrically conductive tip to facilitate cleaning and disinfecting autonomic nervous system sensitivity-point tester 110 between testing uses.

Since electrotherapy needle placement punctures the skin, the medical practitioner may be required to wear gloves during needle placement. Prior sensitivity-point tester designs provide the return signal path via the bare hand of the medical practitioner, which must be placed over a metal contact on the housing of the sensitivity-point tester. In contrast, providing electrode 120 is advantageous over prior sensitivity-point tester designs because the medical practitioner's gloves need not be removed in patient testing theatre 100.

Resistivity measurement 210 and autonomic nervous system stimulator 220 are coupled to switch 230, which may be a double-pole, double-throw switch with positions B, A that selectively couple the electrotherapy signal or the electrical resistance measuring signal respectively to electrically conductive tip 115, while simultaneously coupling the corresponding return signals to electrode 120. Therefore, circuit 110 is in a resistance-measuring mode when switch 230 is in position A and in an autonomic nervous system mode when switch 230 is in position B.

Figure 3:
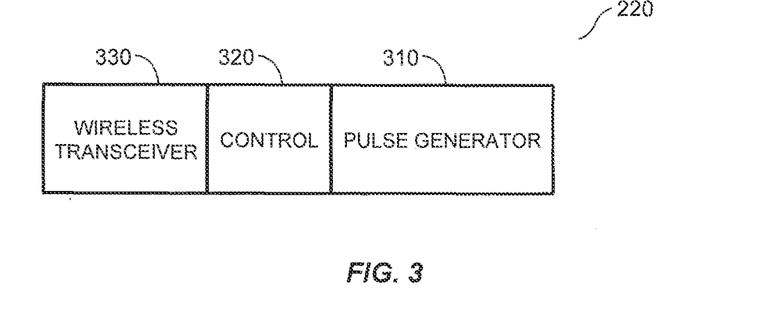
FIG. 3 depicts a simplified block diagram of the autonomic nervous system stimulator represented in FIG. 2, in accordance with one embodiment of the present invention.

FIG. 3 depicts a simplified block diagram of autonomic nervous system stimulator 220 represented in FIG. 2, in accordance with one embodiment of the present invention. FIG. 3 depicts autonomic nervous system stimulator 220, which includes a pulse generator 310, a control unit 320, and a wireless transceiver 330. Pulse generator 310 provides the electrotherapy signal, which includes characteristic such as frequency, amplitude, pulse shape, and duty cycle, which are set by control unit 320. The electrotherapy signal may be similar or identical to the signal used during long-term electrotherapy treatment. Control unit 320 couples to wireless transceiver 330, which may receive characteristic settings from computer 165 and set the characteristics in pulse generator 310. Control unit 320 may also perform power saving functions such as turning off either resistivity measurement 210 or autonomic nervous system stimulator 220 responsive to switch 230 position.

Wireless transceiver 330 need not have high bandwidth or long transmission range capability but because autonomic nervous system sensitivity-point tester 110 may be a handheld portable device, power savings may be desirable to extend battery life. Therefore, wireless transceiver may operate on low bandwidth, power saving radio transmission standards such as Bluetooth®, 6LoWPAN®, ZigBee®, DASH7®, Z-Wave®, MiWi®, or OSION®.

Figure 4A:
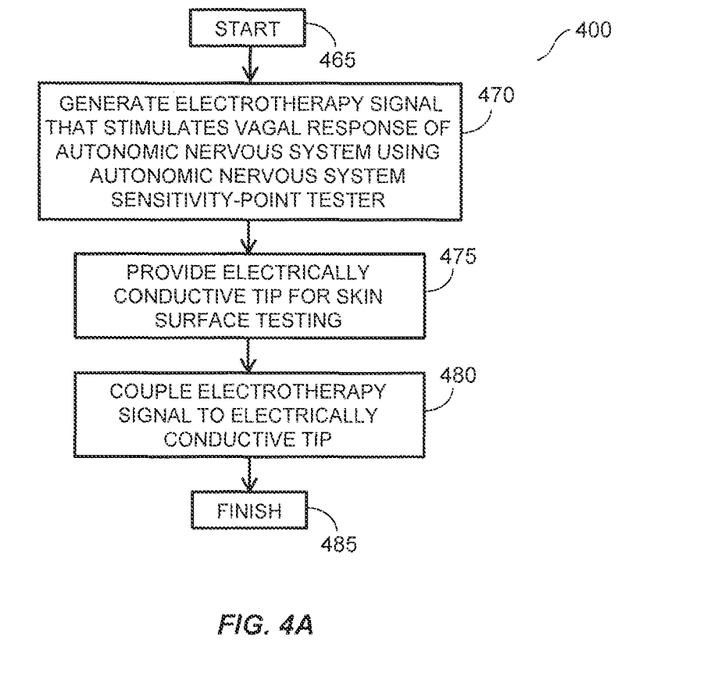
FIG. 4A depicts a simplified flowchart of a method for autonomic nervous system sensitivity-point testing on a skin of a patient, in accordance with one embodiment of the present invention.

FIG. 4A depicts a simplified flowchart of a method 400 for autonomic nervous system sensitivity-point testing on a skin of a patient, in accordance with one embodiment of the present invention. Referring simultaneously to FIG. 2 and FIG. 4A, the method starts 465 by the medical practitioner generating 470 the electrotherapy signal that stimulates a vagal response of an autonomic nervous system of the patient when the patient is tested by using autonomic nervous system sensitivity-point tester 110 in autonomic nervous system mode, i.e. setting switch 230 in position B. The electrically conductive tip 115 is provided 475 that electrically contacts but does not puncture the skin surface when the patient is tested. Setting switch 230 in position B couples 480 the electrotherapy signal to electrically conductive tip 115 as described above. Thus, before finish 485 of this embodiment, the autonomic nervous system sensitivity-point tester 110 is set up to do skin surface testing on the patient.

Figure 4B:
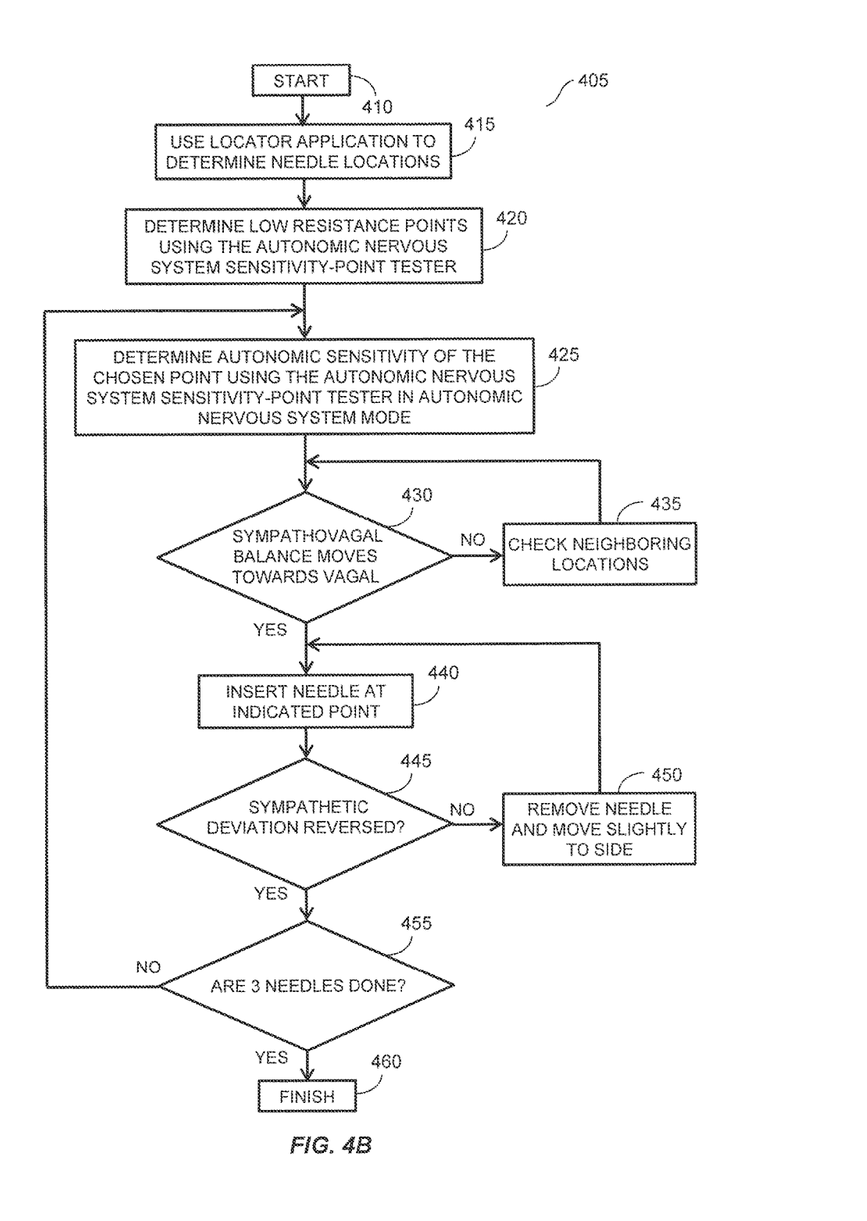
FIG. 4B depicts a simplified flowchart of a method for autonomic nervous system sensitivity-point testing on a skin of a patient, in accordance with another embodiment of the present invention.

FIG. 4B depicts a simplified flowchart of a method 405 for autonomic nervous system sensitivity-point testing on a skin of a patient, in accordance with another embodiment of the present invention. Referring simultaneously to FIG. 1 and FIG. 4B, the method starts 410 in one embodiment, by using 415 a locator application running on computer 165 to generally determine the needle locations. In other words, choosing a first portion of the patient's skin is done by obtaining a preliminary skin location, e.g. on the ear, from graphical user interface 160 coupled to computer 165 executing a program responsive to a symptom of the patient. For example, the patient may be complaining to the medical practitioner of a pain in the lower back. The medical practitioner may select that symptom on graphical user interface 160, which responds by displaying the general location on a map of the ear, where acupuncture electrotherapy has been associated with lower back pain treatment.

Referring simultaneously to FIG. 2 and FIG. 4B, the sensitivity-point location may be further localized by choosing a first portion of skin within the region identified in step 415 by determining 420 low resistance points using autonomic nervous system sensitivity-point tester 110 operating in resistance measuring mode, i.e. by setting switch 230 in position A. Then resistivity measurement 210 generates the electrical resistance-measuring signal, which is coupled to electrically conductive tip 115. Electrode 120 is applied to a second portion of skin, the electrode being a return signal path for the resistance-measuring signal The medical practitioner may then apply the electrical resistance measuring signal to the first portion of skin with electrically conductive tip 115 that electrically contacts but does not puncture the skin when the patient is tested. The electrical resistance at the first portion of skin is measured by resistivity measurement 210 and causes indicator 215 to provide an indication responsive to a value of skin resistivity 225, i.e. changing an emitted sound pitch correlated with the value. The medical practitioner moves or probes the electrically conductive tip on the skin surface in response to the indication to selectively find a low resistance location of skin near the first portion of skin.

The medical practitioner may then further optimize the electrotherapy needle insertion location by determining 425 the autonomic sensitivity of the chosen point using autonomic nervous system sensitivity-point tester 110 in autonomic nervous system mode, i.e. by setting switch 230 in position B. Then autonomic nervous system stimulator 220 generates the electrotherapy signal, which is coupled to electrically conductive tip 115. Electrode 120 is applied, if not already applied during step 420, to another portion of skin, the electrode being a return signal path for the electrotherapy signal.

The medical practitioner may then apply the electrotherapy signal to the selected portion of skin with electrically conductive tip 115 that electrically contacts but does not puncture the skin when the patient is tested. The electrotherapy signal may stimulate a vagal response of the autonomic nervous system of the patient when electrically conductive tip 115 is located in contact with an autonomic nervous system sensitivity-point on the skin surface when the patient is tested. Referring simultaneously to FIG. 1 and FIG. 4B, to measure the autonomic nervous system, the medical practitioner couples autonomic nervous system monitor 135 to the patient as described above. Autonomic nervous system monitor 135 analyzes a state of the autonomic nervous system of the patient from a time-varying signal representing a chaotic series of time intervals between quasi-periodical events produced by a cardiac system of the patient, i.e. from the patient's electrocardiogram. Autonomic nervous system monitor 135 also measures and displays a first sympathovagal balance of the patient.

Figure 5:
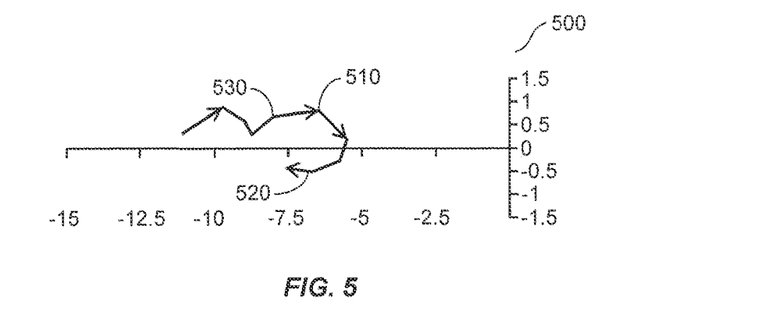
FIG. 5 depicts an exemplary response of a sympathovagal balance used in the method represented in FIG. 4B.

FIG. 5 depicts an exemplary response of a sympathovagal balance 500 used in method 425 represented in FIG. 4B. FIG. 5 depicts sympathovagal balance 500, which plots balance trajectory 530 for the patient in real time as shown by the series of arrows on the balance trajectory. The horizontal axis represents a parasympathetic or vagal response in the direction towards higher negative numbers, i.e. towards the left direction on the plot. Conversely, a sympathetic response is represented on the plot's horizontal axis in the direction of smaller negative numbers, i.e. towards the right of the plot. A sympathetic trending balance trajectory 530 over time indicates increasing pain or dysfunction, while a vagal trending balance trajectory indicates pain relief. In this example, the patient may be suffering anxiety to the clinical setting and the patient's balance trajectory 530 starts out generally moving away from the parasympathetic or vagal part of the horizontal axis and towards the sympathetic direction as indicated at point 510.

Referring simultaneously to FIG. 4B and FIG. 5, the medical practitioner determines 430 a response outcome based on the sympathovagal balance. The response outcome is positive when the sympathovagal balance moves towards the vagal response as shown at point 520 indicating the electrically conductive tip 115 is positioned optimally on the skin surface and the patient's autonomic nervous system is responding favorably to the electrotherapy signal. In contrast, the response outcome is negative when the sympathovagal balance does not move towards the vagal response.

When the response outcome is negative, the medical practitioner checks 435 or chooses a slightly different neighboring portion of skin of the patient abutting the earlier portion of chosen skin. The medical practitioner repeats applying the electrotherapy signal, measuring the sympathovagal balance, and determining the response outcome until the response outcome is positive or until a certain predetermined number of portions of skin are tested or time has elapsed.

When the response outcome is positive, the medical practitioner inserts 440 an electrotherapy needle at that portion of skin. The electrotherapy needle location selected with the procedure described above has been tested earlier at step 430 raising the confidence that the same electrotherapy signal applied to that location during the treatment regimen should have the desired beneficial effect on the patient's autonomic nervous system.

The needle insertion will cause a little pain creating a sympathetic deviation such as shown at point 510 on balance trajectory 530 that should quickly subside or reverse. However, the needle insertion location may be at a point that will stimulate an undesired long-term pain response. Therefore, after needle insertion, the medical practitioner measures a second sympathovagal balance of the patient to determine 445 a sympathetic deviation reversal outcome based on the second sympathovagal balance. The reversal outcome is positive when the second sympathovagal balance reverses from a sympathetic response towards a vagal response as shown at point 520 on balance trajectory 530. The reversal outcome is negative when the second sympathovagal balance does not reverse from a sympathetic response towards a vagal response.

When the reversal outcome is negative, the medical practitioner removes 450 the electrotherapy needle from the portion of skin and moves the needle slightly to the side to choose another portion of skin abutting the earlier portion of skin. The medical practitioner repeats inserting, measuring the second sympathovagal balance, and determining the reversal outcome until the reversal outcome is positive or until a certain predetermined number of portions of skin are tested or time has elapsed.

The electrotherapy treatment may require more than one stimulation point on the patient's ear. For example, one point may be stimulated to address lower back pain and another point may be stimulated for general pain relief. Accordingly, when the reversal outcome at step 445 is positive, the medical practitioner determines 455 a number of inserted electrotherapy needles. The testing is finished 460 when the number of inserted electrotherapy needles is equal to a predetermined number of electrotherapy needles required for the electrotherapy treatment, e.g. three stimulation needles—one needle located for a specific symptom and two needles located at two different locations for general pain relief. When a number of inserted electrotherapy needles is less than the predetermined number of electrotherapy needles, the medical practitioner repeats choosing the location, applying the electrotherapy signal, measuring the first sympathovagal balance, determining the response outcome, inserting the needle, measuring the second sympathovagal balance, and determining the reversal outcome.

Figure 6:
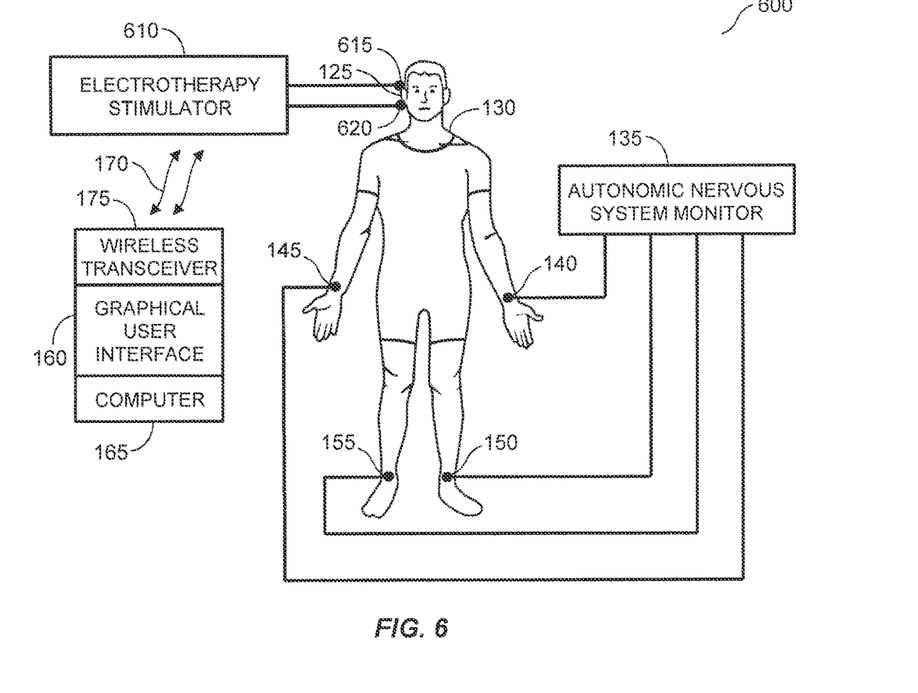
FIG. 6 depicts a simplified block diagram of a patient treatment theatre, in accordance with one embodiment of the present invention.

FIG. 6 depicts a simplified block diagram of a patient treatment theatre 600, in accordance with one embodiment of the present invention. Patient treatment theatre 600 includes the same elements as patient testing theatre 100 represented in FIG. 1 except autonomic nervous system sensitivity-point tester 110, electrically conductive tip 115, and electrode 120, are replaced in FIG. 6 by an electrotherapy stimulator 610, an electrotherapy needle 615, and an electrically conductive electrode 620. Electrotherapy needle 615 and electrically conductive electrode 620 are coupled to electrotherapy stimulator 610. In contrast to electrically conductive tip 115, which includes a small but dull tip that prevents skin puncture, electrotherapy needle 615 includes a short, sharp-tipped electrically conductive electrode needle adapted to electrically contact and puncture a portion of the skin surface to inject the electrotherapy signal below the skin surface.

The location where electrotherapy needle 615 is located on ear 125 may be determined by the procedures outlined earlier referenced in FIG. 4A and FIG. 4B using the autonomic nervous system sensitivity-point tester 110 referenced in FIG. 1 and FIG. 2. Unlike autonomic nervous system sensitivity-point tester 110, which may be a hand-held device used only for testing the location of electrotherapy needle placement, electrotherapy stimulator 610 may be a wearable device that is attached to the patient for a prolonged period of time to deliver electrotherapy signals to the needles emplaced in the skin. Autonomic nervous system monitor 135 may be attached to the patient during the placement of electrotherapy needle 615 but may be disconnected from the patient during the electrotherapy treatment regimen, thus providing mobility for the patient during treatment. Wireless transceiver 175, graphical user interface 160 and computer 165 may be as referenced in FIGS. 1, 2, and 3, to pass electrotherapy signal characteristics to electrotherapy stimulator 610 during set up when the needles are placed into the skin.

Referring to FIG. 6, electrically conductive electrode 620 may be similar to electrode 120 and is adapted to electrically contact but not puncture a different portion of the skin surface than where electrotherapy needle 615 is inserted. Electrically conductive electrode 620 may provide a direct electrical contact between a surface of electrically conductive electrode 620 and the skin surface thereby providing a return signal path for the electrotherapy signal when the periodic signal is injected below the skin surface. The direct electrical contact avoids signal degradation when adhesive glue is instead used between the skin and the electrode. Electrically conductive electrode 620 may be taped to the skin for a prolonged attachment time. Electrically conductive electrode 620 may include a short strip of metal foil that is coupled to electrotherapy stimulator 610 via a flexible wire. Alternatively, electrically conductive electrode 620 may include a thin flexible braided wire directly coupled to electrotherapy stimulator 610.

Figure 7:
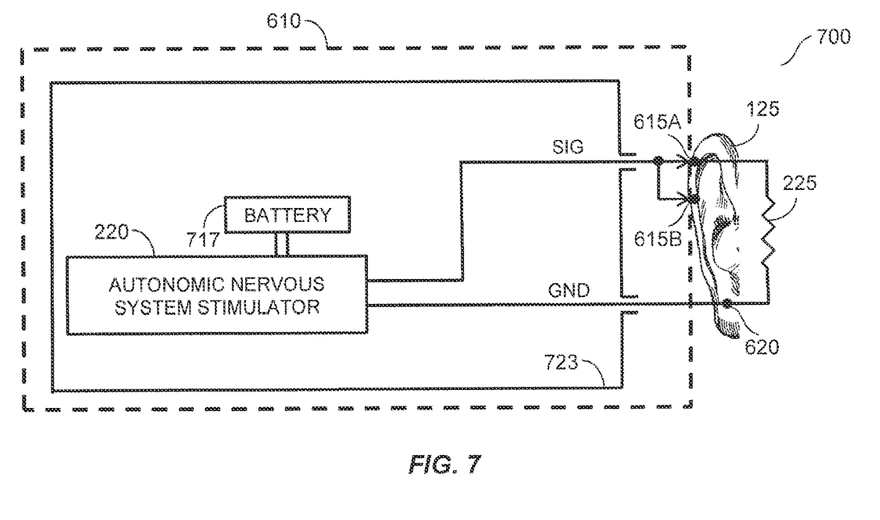
FIG. 7 depicts a simplified block diagram of the electrotherapy stimulator and the portion of the patient's skin represented in FIG. 6, in accordance with one embodiment of the present invention.

FIG. 7 depicts a simplified block diagram of the electrotherapy stimulator 610 and the portion of the patient's skin 125 represented in FIG. 6, in accordance with one embodiment of the present invention. FIG. 7 depicts electrotherapy stimulator 610, which includes autonomic nervous system stimulator 220, one or more electrotherapy needles 615A, 615B, a battery 717, a housing 723, and an electrode 620. Battery 717 provides portable power to the circuit and enables prolonged operation. Autonomic nervous system stimulator 220 previously described and referenced in FIG. 2 and FIG. 3 may be similar to autonomic nervous system stimulator 220 included in electrotherapy stimulator 610 depicted in FIG. 7. The one or more electrotherapy needles 615A, 615B may be coupled in parallel to the electrotherapy signal (SIG) line output of autonomic nervous system stimulator 220.

Housing 723 may have an insulating surface and at least one orifice in the insulating surface, the electrotherapy needles 615A may be located outside the housing and coupled through the orifice to the autonomic nervous system stimulator circuit. Housing 723 may hermetically seal or enclose the battery and the autonomic nervous system stimulator circuit. Housing 723 may have a shape being adapted to conform to a portion of the skin surface when the periodic signal is injected below the skin surface. For example, the shape of the housing may have a flat surface when electrotherapy stimulator 610 is mounted on a flat portion of skin or may have a contoured surface when mounted on a portion of skin having a contour. Housing 723 may be attached to the skin via tape or adhesive. For example, housing 723 may be attached by an adhesive layer to the skin on the head behind and below the ear with flexible wires reaching around the ear to the front of the ear surface where electrotherapy needles 615A, 615B are attached. Electrode 620 may be taped to the skin surface on the inside or back surface of the ear facing the head.

Figure 8:
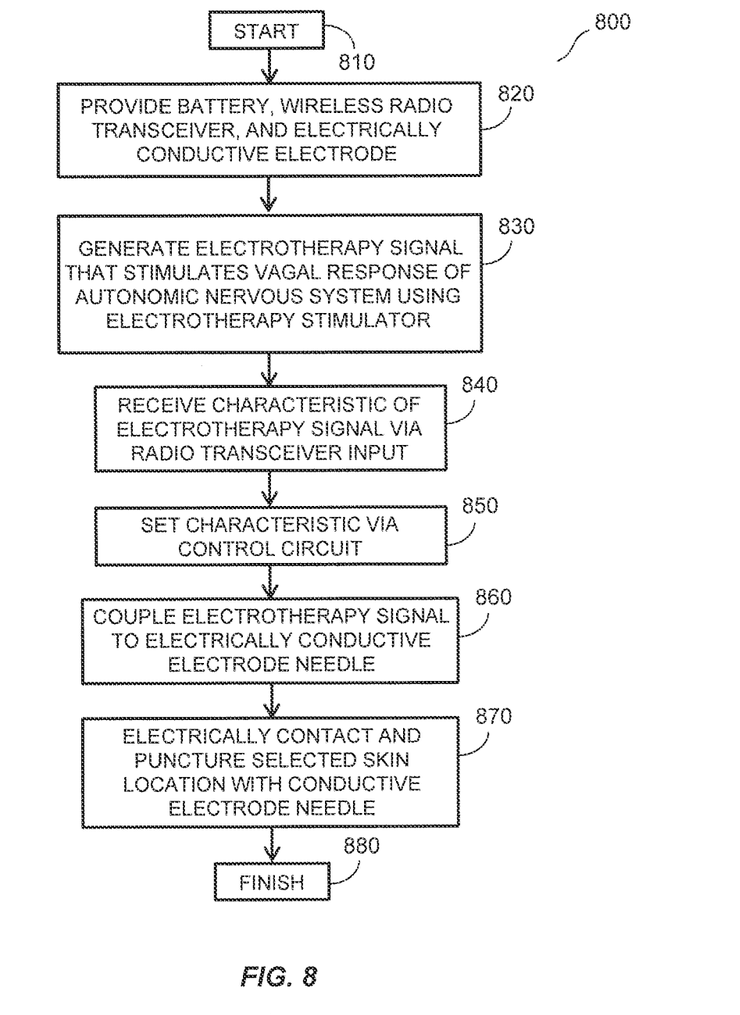
FIG. 8 depicts a simplified flowchart of a method for electrotherapy signal injection into a skin of a patient, in accordance with another embodiment of the present invention.

FIG. 8 depicts a simplified flowchart of a method 800 for electrotherapy signal injection into a skin of a patient, in accordance with another embodiment of the present invention. Referring simultaneously to FIGS. 3, 6, 7, and 8, the method starts 810 by providing 820 battery 717, wireless radio transceiver 330, and one or more electrotherapy needles 615A, 615B. The electrotherapy signal is a periodic signal in time that stimulates a vagal response of the autonomic nervous system of the patient is generated 830 using the circuit in electrotherapy stimulator 610. Electrotherapy stimulator 610 may receive 840 a characteristic of the periodic signal via an input of wireless transceiver 330. Control circuit 320 may then set 850 the characteristic into the circuit of pulse generator 310.

The periodic electrotherapy signal is coupled 860 to electrotherapy needle 615. The periodic signal is injected below the portion of the skin surface by electrically contacting and puncturing 870 the skin surface when electrotherapy needle 615 is inserted into the skin by the medical practitioner. The location of the needle insertion may be determined using the method described in reference to FIGS. 4A, 4B and the autonomic nervous system sensitivity-point tester 110 described in reference to FIGS. 1, 2, and 3. After the electrotherapy needles are set in the skin, the electrotherapy stimulator is attached to the patient, and the patient's autonomic nervous system is checked. Then, autonomic nervous system monitor 135 may be disconnected, and the patient may go about his or her routine activities while electrotherapy stimulator 610 delivers periodic pulses that stimulate a vagal response of the autonomic nervous system over a predetermined and/or extended therapy time.

When a round of electrotherapy is done, the patient may return for further monitoring by the medical practitioner using autonomic nervous system monitor 135 to quantitatively determine the treatment outcome by comparing quantitative measurements of the patient's autonomic nervous system before and after the treatment round. The settings of electrotherapy stimulator 610 may be adjusted between the electrotherapy treatment rounds to optimize treatment. For example, the amplitude of the electrotherapy signal may be increased by the medical practitioner as treatment progresses due to desensitization of the nerves at the electrotherapy needle sites, as determined by quantitatively monitoring the patient using autonomic nervous system monitor 135.

Figure 9:
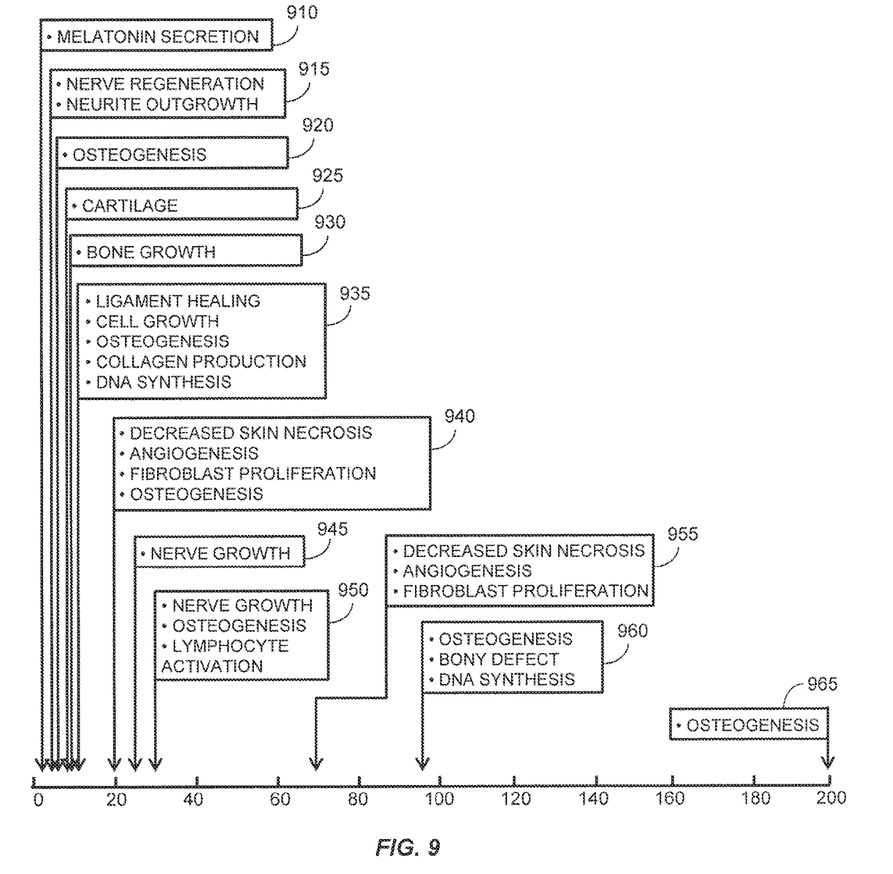
FIG. 9 depicts a chart showing patient responses to electrotherapy signal injection versus electrotherapy signal frequency from peer-reviewed literature.

Electrotherapy signal characteristics may affect treatment outcomes. For example, FIG. 9 depicts a chart showing patient responses to electrotherapy signal injection versus electrotherapy signal frequency from peer-reviewed literature. The frequency characteristic is shown along the horizontal axis in a range below 200 Hz. The following therapeutic responses have been observed in ascending frequency order in the range between 1 Hz and 10 Hz respectively; melatonin secretion 910, nerve regeneration, neurite outgrowth 915, osteogenesis 920, cartilage 925, bone growth 930, ligament healing, cell growth, osteogenesis, collagen production, and deoxyribonucleic acid (DNA) synthesis 935. At about 20 Hz decreased skin necrosis, angiogenesis, fibroblast proliferation, and osteogenesis 940 have been observed. At about 25 Hz nerve growth 945 has been observed. Nerve growth, osteogenesis, and lymphocyte activation 950 have been observed at about 30 Hz. Decreased skin necrosis, angiogenesis, and fibroblast proliferation have also been observed at about 70 Hz. Osteogenesis, bony defect, and DNA synthesis 960 have been observed at about 95 Hz. Osteogenesis 965 has also been observed at about 200 Hz. Accordingly, setting the frequency characteristic of the periodic signal generated by pulse generator 310 to a predetermined frequency associated with a therapeutic response mode of the patient may improve or accelerate electrotherapy treatment outcome.

The above embodiments of the present invention are illustrative and not limiting. Various alternatives and equivalents are possible. Although, the invention has been described with reference to a human patient by way of an example, it is understood that the invention is not limited by the type of patient so long as the patient has an autonomic nervous system and cardiac system. Although, the invention has been described with reference to auricular acupuncture electrotherapy by way of an example, it is understood that the invention is not limited by the location of the skin portion being tested or treated so long as the location has autonomic nervous system sensitivity-points. Other additions, subtractions, or modifications are obvious in view of the present disclosure and are intended to fall within the scope of the appended claims.

What is claimed is:

1. An electrical system, consisting essentially of:
   an electrotherapy stimulator, comprising:
      a battery;
      a circuit adapted to generate a periodic signal;
      a wireless radio transceiver;
      a control circuit adapted to set a characteristic of the periodic signal, the characteristic being received by an input of the wireless radio transceiver;
      a first stimulating electrically conductive electrode adapted to electrically contact and puncture a first portion of a surface of the patients ear, wherein the periodic signal is configured to be coupled to the first electrically conductive electrode and is configured to cause a monitorable change in the sympathovagal balance between the parasympathetic and the sympathetic components of the autonomic nervous system (ANS) of the patient;
      a second stimulating electrically conductive electrode adapted to electrically contact but not puncture a second portion of a surface of the patient's ear; and
   an electronic ANS monitor, configured to monitor, a third portion of a surface of the patient, the sympathovagal balance between the parasympathetic and the sympathetic components of the ANS of the patient based on a time-varying signal representing a chaotic series of time intervals between quasi-periodic events produced by a cardiac system of the patient and to provide an indication of the monitorable change in the sympathovagal balance caused by the periodic signal;
   wherein the third portion of the surface of the patient monitored by the electronic ANS monitor is a skin of an arm or a leg.

2. The electrical apparatus of claim 1, the second stimulating electrically conductive electrode provides a direct electrical contact between the second stimulating electrically conductive electrode and the second portion of the surface thereby providing a return signal path for the periodic signal when the periodic signal is injected below the first portion of the surface.

3. The electrical apparatus of claim 1 further consisting of a housing having an insulating surface and at least a first orifice in the insulating surface, the first electrically conductive electrode adapted to be located outside the housing and coupled through the first orifice to the circuit, the housing enclosing the battery and the circuit.

4. The electrical apparatus of claim 3, wherein the housing is adapted to have a shape being adapted to conform to the second portion of the surface when the periodic signal is injected below the first portion of the surface.

5. The electrical apparatus of claim 3, wherein the housing is adapted to hermetically seal the electrical apparatus.

6. The electrical apparatus of claim 1, wherein the wireless radio transceiver operates on a transmission standard selected from the group consisting of Bluetooth®, 6LoWPAN®, ZigBee®, DASH7®, Z-Wave®, MiWi®, and OSION®.

7. The electrical apparatus of claim 1, wherein the characteristic is selected from the group consisting of a frequency, an amplitude, a pulse shape, and a duty cycle.

8. The electrical apparatus of claim 1, wherein the periodic signal is an electrotherapy signal, the characteristic of the periodic signal is adapted to stimulate a response in a parasympathetic nervous system of a patient, and the second portion of the surface is a skin of the patient when the periodic signal is injected below the first portion of the surface.

9. The electrical apparatus of claim 1, wherein the frequency of the periodic signal is set to a predetermined frequency associated with a treatment of a patient.

10. The electrical apparatus of claim 1, wherein the third portion of the surface is on a right arm, a left arm, a right leg, or a left leg of the patient.

11. A method for signal injection consisting essentially of:
generating a periodic signal;
wirelessly receiving a characteristic of the periodic signal;
setting the characteristic of the periodic signal via a control circuit;
coupling the periodic signal to a first stimulating electrically conductive electrode;
with the first stimulating electrically conductive electrode, electrically contacting a patient through puncturing a first portion of a surface of the patients ear;
coupling the periodic signal to the first electrically conductive electrode to cause a monitorable change in the sympathovagal balance between the parasympathetic and the sympathetic components of the autonomic nervous system (ANS) of the patient;
contacting but not puncturing a second portion of a surface by a second stimulating electrically conductive electrode;
with an electronic ANS monitor, monitoring from a third portion of a surface of the patient the sympathovagal balance between the parasympathetic and the sympathetic components of the ANS of the patient based on a time-varying signal representing a chaotic series of time intervals between quasi-periodic events produced by a cardiac system of the patient; with the electronic ANS monitor, providing an indication of the monitorable change in the sympathovagal balance caused by the periodic signal, wherein the third portion of the surface of the patient being monitored by the electronic ANS monitor is a skin of an arm or a leg; and
resetting the characteristic of the periodic signal via the control circuit, wherein the characteristic is reset based at least in part on the change.

12. The method of claim 11 further consisting of:
wherein the second stimulating electrically conductive electrode provides a direct electrical contact between the second stimulating electrically conductive electrode and the second portion of the surface, thereby providing a return signal path for the periodic signal when the periodic signal is injected below the first portion of the surface.

13. The method of claim 11 further consisting of:
providing a housing having an insulating surface and at least a first orifice in the insulating surface;
locating the first stimulating electrically conductive electrode outside the housing;
coupling the first stimulating electrically conductive electrode through the first orifice to the circuit; and
enclosing the battery and the circuit with the housing.

14. The method of claim 13 further consisting of:
shaping the housing to conform to the second portion of the surface when the periodic signal is injected below the first portion of the surface.

15. The method of claim 13 further consisting of:
hermetically sealing the electrical apparatus with the housing.

16. The method of claim 11 further consisting:
operating the wireless radio transceiver on a transmission standard selected from the group consisting of Bluetooth®, 6LoWPAN®, ZigBee®, DASH7®, Z-Wave®, MiWi®, and OSION®.

17. The method of claim 11 further consisting of:
selecting the characteristic from the group consisting of a frequency, an amplitude, a pulse shape, and a duty cycle.

18. The method of claim 11, wherein the periodic signal is an electrotherapy signal, the characteristic of the periodic signal stimulating a response in a parasympathetic nervous system of a patient, and the second portion of the surface is a skin of the patient when the periodic signal is injected below the first portion of the surface.

19. The method of claim 11 further consisting of:
setting the frequency of the periodic signal to a predetermined frequency associated with a treatment of a patient.

20. The method of claim 11, wherein the third portion of the surface is on a right arm, a left arm, a right leg, or a left leg of the patient.

* * * * *